United States Patent [19]

Minagawa et al.

[11] Patent Number: 4,798,836
[45] Date of Patent: Jan. 17, 1989

[54] BIS-(2,2,6,6-TETRAMETHYL-PIPERIDYL) DIIMIDES AS LIGHT STABILIZERS FOR SYNTHETIC POLYMERS

[75] Inventors: Motonobu Minagawa, Koshigaya; Yutaka Nakahara, Okegawa; Bunji Hirai, Kuki; Kazuo Sugibuchi, Tokyo, all of Japan

[73] Assignee: Adeka Argus Chemical Co., Ltd., Urawa, Japan

[21] Appl. No.: 113,296

[22] Filed: Oct. 26, 1987

[51] Int. Cl.$^4$ .................. C08K 5/34; C07D 401/04
[52] U.S. Cl. ........................... 524/89; 524/83; 524/84; 524/99; 524/100; 524/102; 524/111; 524/118; 524/119; 524/120; 524/141; 524/148; 524/151; 524/153; 524/157; 524/171; 524/316; 524/321; 524/324; 524/326; 524/330; 524/334; 524/335; 524/336; 524/337; 546/81; 546/87
[58] Field of Search .............. 524/89, 102, 83, 84, 524/111, 118, 119, 120, 141, 148, 151, 153, 157, 171, 316, 321, 324, 326, 330, 334, 335, 336, 337, 338; 546/81, 87

[56] References Cited

U.S. PATENT DOCUMENTS

| | | | |
|---|---|---|---|
| 3,781,237 | 12/1973 | Alvino et al. | 524/102 |
| 4,001,181 | 1/1977 | Ramey et al. | 524/91 |
| 4,191,683 | 3/1980 | Brunetti et al. | 524/102 |
| 4,198,334 | 4/1980 | Rasberger | 524/102 |
| 4,356,307 | 10/1982 | Kelkenberg et al. | 524/102 |
| 4,396,735 | 8/1983 | Minagawa et al. | 524/92 |
| 4,594,375 | 6/1986 | Krishnan et al. | 524/89 |
| 4,609,699 | 9/1986 | Meyer et al. | 524/89 |
| 4,721,736 | 1/1988 | Rei et al. | 524/89 |

*Primary Examiner*—Kriellion Morgan

[57] ABSTRACT

Bis-(2,2,6,6-tetramethyl-piperidyl)diimides are provided, having the formula:

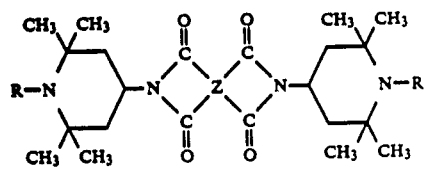

in which R is selected from the group consisting of hydrogen; oxyl; alkyl and alkenyl having from one to about eighteen carbon atoms; epoxy and hydroxyalkyl having from two to about eight carbon atoms; acyl having from two to about eight carbon atoms; and phenalkyl having from seven to about twelve carbon atoms; and Z is a tetravalent aliphatic or cycloaliphatic hydrocarbon group having from two to about eighteen carbon atoms; and stabilizer and synthetic polymer compositions containing such diimides having improved resistance to deterioration when exposed to light.

16 Claims, No Drawings

BIS-(2,2,6,6-TETRAMETHYL-PIPERIDYL) DIIMIDES AS LIGHT STABILIZERS FOR SYNTHETIC POLYMERS

Polymers such as polyethylene, polypropylene, polyvinylchloride, etc. are subject to degradation upon exposure to light, and discoloration, resulting in a deterioration of mechanical strength.

Therefore various light stabilizers have been used to inhibit such deterioration. However, the available conventional stabilizers are unsatisfactory in stabilizing effect, unstable to heat and oxidation, and easily extracted by water or organic solvents. Some conventional stabilizers impart color to the polymers.

Among the conventional stabilizers, hindered piperidine compounds do not impart color to the polymer, and therefore, hindered piperidine compounds are widely used as light stabilizers.

Murayama et al U.S. Pat. No. 3,904,581, patented Sept. 9, 1975, discloses synthetic polymer compositions which comprise a 4-aminopiperidine derivative having the following formula

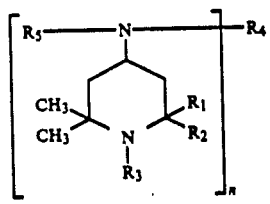

wherein $R_1$ and $R_2$ represent a lower alkyl group or $R_1$ and $R_2$ together with the carbon atom to which they are attached represents a group

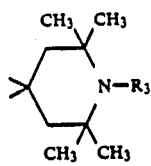

$R_3$ represent an alkyl group, a substituted alkyl group, an alkenyl group, an alkynyl group or an unsubstituted or substituted aralkyl group. n is an integer of 1, 2 or 3.

When n is 1, $R_4$ represents a hydrogen atom, an alkyl group, a substituted alkyl group, an alkenyl group, an alkynyl group, a substituted or unsubstituted aralkyl group, a cycloalkyl group, a substituted or unsubstituted aryl group, a monoacyl group, an alkoxycarbonyl group which may be substituted with hydroxyl, an aralkoxycarbonyl group, an N-substituted or unsubstituted carbamoyl group, an N-substituted or unsubstituted thiocarbamoyl group or a monovalent group from an oxoacid, or $R_4$ and $R_5$ together with the nitrogen atom to which they are attached, represent a phthalimido group.

When n is 2, $R_4$ is an alkylene group, an alkenylene group, an aralkylene group, an arylene group, a diacyl group, a carbonyl group, an N-substituted dicarbamoyl group, an N-substituted bisthiocarbamoyl group or a divalent group from an oxoacid, or $R_4$ and $R_5$ together with the nitrogen atom to which they are attached, represent a pyromellitodiimido group.

German Offenlegungsschrift (application laid open to public inspection) No. 2,040,975 discloses compounds having the following formula as light stabilizers for synthetic polymers

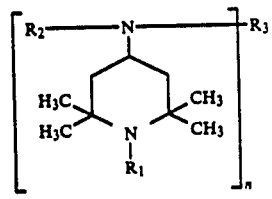

wherein $R_1$ represent a hydrogen atom or an acyl group; $R_2$ represents a hydrogen atom, an unsubstituted or substituted alkyl group, a cycloalkyl group, an unsubstituted or substituted aralkyl group or the group of the formula

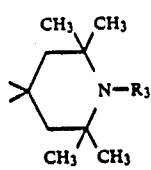

n is an integer of 1 to 3 inclusive; and, when is is 1, $R_3$ represents a hydrogen atom, an acyl group, an alkoxycarbonyl group, a carbamoyl group, a thiocarbamoyl group, an N-substituted carbamoyl group, an N-substituted thiocarbamoyl group or a monovalent group derived by removing one hydroxyl group from an oxoacid or $R_3$ may form, together with $R_2$ the group of the formula

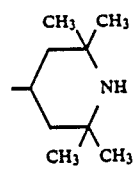

when n is 2, $R_3$ represents a diacyl group, an N-substituted dicarbamoyl group, an N-substituted bisthiocarbamoyl group, a carbonyl group or a divalent group derived, by removing two hydroxyl groups, from an oxoacid, and, when n is 3, $R_3$ represents a triacyl group, an N-substituted tricarbamoyl group, an N-substituted tristhiocarbamoyl group or a trivalent group derived, by removing three hydroxyl groups, from an oxoacid or a salt thereof.

Ramey et al U.S. Pat. No. 4,001,181, patented Jan. 4, 1977, discloses compounds having the formula

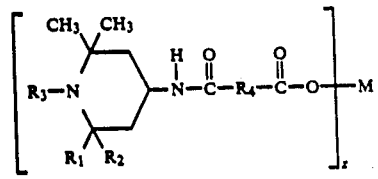

wherein
$R_1$ and $R_2$ are lower alkyl or form a cycloalkyl ring.

R₃ is hydrogen, alkyl, β-methoxyethyl, alkenyl, propargyl, benzyl or alkyl substituted benzyl, R₄ is alkylene, alkyl-thio-alkyl or alkyl-oxo-alkyl.

M is hydrogen or a metal, and z is an integer of from 1 to 4, are good stabilizers against actinic radiation.

These compounds are prepared, for example, from 4-amino-2,2,6,6-tetramethylpiperidine and succinic anhydride to give N-(2,2,6,6-tetramethylpiperidyl-4)succinamic acid. The metal salts of the acids are readily prepared by reacting the acids or their salts with a reactive form of the metal or metal complex.

Brunetti et al, U.S. Pat. No. 4,191,683, patented Mar. 4, 1980, discloses higher alkylated 4-aminopiperidine derivatives defined by the formula

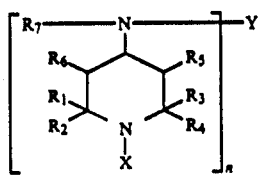

or mixtures of isomers thereof or acid addition salts thereof, wherein

R₁ and R₃ are each ethyl,

R₂ and R₄ are each methyl,

R₅ is methyl and

R₆ is hydrogen whereby R₅ and R₆ are interchangeable,

X is hydrogen, an oxyl radical, alkyl having 1 to 8 C-atoms, alkenyl having 3 to 8 C-atoms, aralkyl having 7 to 8 carbon atoms, an aliphatic acyl group having 7 to 12 C-atoms, or one of the groups —CH₂COOR₈, —CH₂CH(R₉)—OH and —CONHR₁₀, R₇ is hydrogen, alkyl having 1 to 12 C-atoms, cycloalkyl having 5 to 7 C-atoms or aralkyl having 7 to 8 C-atoms, and, if n is 2 and Y is alkylene having 2 to 10 C-atoms, 2-butenylene, arylene having 6 to 12 C-atoms, meta- or para-xylylene or 1,4-cyclohexylene, R₇ is hydrogen, a group —CO—R₁₁ or a group —CO—R₁₂—COOH, R₈ is alkyl having 1 to 8 C-atoms or phenyl, R₉ is hydrogen, methyl or phenyl, R₁₀ is alkyl having 1 to 12 C-atoms, phenyl or cyclohexyl, R₁₁ is hydrogen, alkyl having 1 to 17 carbon atoms, alkenyl having 2 to 5 C-atoms, alkoxy having 1 to 8 C-atoms or phenyl, R₁₂ is

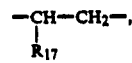

—CH=CH—; —(CH₂)₃—, o-phenylene or o-cyclohexylene, n is 1, 2 or 3,

Y, if n is 1, represents hydrogen, —CH₂CH₂OH, a group —CO—R₁₃,

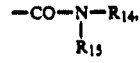

—SO₂—R₁₆, —CO—R₁₂—COOH, —CO—R₁₂—COOMe or

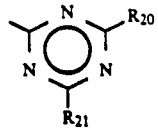

or Y and R₇ together with the N-atom to which they are attached form a succinimide ring which is unsubstituted or substituted by alkyl having 1 to 12 carbon atoms, a maleimide, dimethylmaleimide, phthalimide, tetrahydrophthalimide or hexahydrophthalimide ring, and, if n is 2, Y represents —CO—, —CO—CO—, —CO—R₁₈—CO—, —CONH—R₁₉—NHCO— or

Preferred compounds of formula I are those wherein if n is 1 Y and R₇ together with the N-atom to which they are attached form a succinimide, maleimide, dimethylmaleimide or phthalimide ring, and if n is 2, Y represents —CO—, —CO—CO—, —CO—R₁₈—CO— or —CONH—R₁₉—NHCO—.

Rasberger U.S. Pat. No. 4,198,334, patented Apr. 15, 1980 discloses new esters of hydroxybenzylmalonic acids of the formula

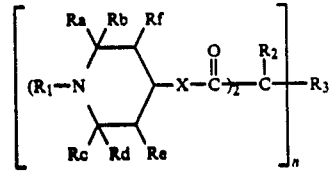

and the acid addition salts thereof, wherein n is 1 or 2,

Ra represents alkyl having 1–6 carbon atoms,

Rb represents alkyl having 1–6 carbon atoms,

Rc represents alkyl having 1–9 carbon atoms, phenyl, benzyl or phenylethyl,

Rd represents alkyl having 1–6 carbon atoms, or

Rc and Rd together represent tetra- or pentamethylene,

Re represents hydrogen, alkyl having 1–5 carbon atoms, alkenyl or alkynyl having 3–4 carbon atoms or aralkyl having 7–8 carbon atoms, Rf represents hydrogen, alkyl having 1–5 carbon atoms, alkenyl or alkynyl having 3–4 carbon atoms, or aralkyl having 7–8 carbon atoms, with Re and Rf being mutually exchangeable, and X represents oxygen or —NR—, R represents hydrogen, alkyl having 1–18 carbon atoms, alkenyl having 3–4 carbon atoms, alkynyl having 3–4 carbon atoms, cycloalkyl having 5–12 carbon atoms, aryl having 6–10 carbon atoms, or aralkyl having 7–9 carbon atoms.

Minagawa et al U.S. Pat. No. 4,396,735, patented Aug. 2, 1983, discloses light stabilizers for synthetic resin compositions, comprising (1) at least one hindered heterocyclic amine having the formula:

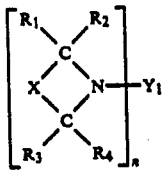

wherein:

X is a bivalent linking radical forming with the ring structure

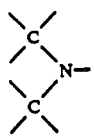

a nitrogen-containing heterocyclic ring having from five to seven ring atoms, preferably piperidine;

$R_1$ and $R_2$ are each selected from the group consisting of lower alkyl, preferably methyl, and $R_1$ and $R_2$ taken together as pentylene $(CH_2)_5$;

$R_3$ and $R_4$ are each selected from the group consisting of lower alkyl, and $R_3$ and $R_4$ taken together as one of butylene $-(CH_2)_4$, pentylene $-(CH_2)_5$, and $CH_2-C(CH_3)_2-NH-C(CH_3)_2-CH_2-$;

n is 1 or 2; and when n is 1, $Y_1$ is selected from the group consisting of hydrogen, O, OH, alkyl, alkenyl, alkynyl, aralkyl and acyl having from one to about thirty carbon atoms; and when n is 2, $Y_1$ is selected from the group consisting of alkylene, alkenylene, alkynylene, cycloalkylene and aralkylene having from one to about thirty carbon atoms; together with (2) at least one heterocyclic acid hydrazide having the formula:

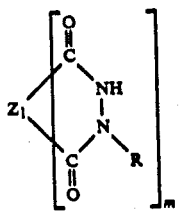

wherein:

R is selected from the group consisting of hydrogen, alkyl, aryl and such groups having hydroxyl, carboxylic acid ester, oxyether and carbonyl groups having from one to about thirty carbon atoms;

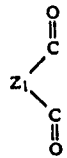

is the residue of a dicarboxylic or tetracarboxylic acid, wherein Z is selected from the group consisting of alkylene, alkenylene, cycloalkylene, alkylcycloalkylene, arylene and alkylarylene having from one to about thirty carbon atoms, and such radicals bearing free carboxylic acid or carboxylic acid ester groups; and m is 1 or 2.

In such combinations, the heterocyclic acid hydrazide, which alone is not a light stabilizer, synergizes the stabilizing effectiveness of the hindered heterocyclic amine.

U.S. Pat. No. 4,356,307, patented Oct. 26, 1982, to Kelkenberg and Wolf discloses cyclic imides of the formula:

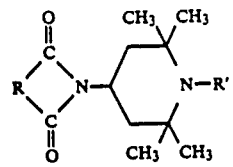

in which R represents a saturated or unsaturated, optionally alkyl- or alkenyl-substituted alkylene or cycloalkylene radical having 2-120 C-atoms and R' represents hydrogen or a substituent selected from the group consisting of an alkyl radical having 1-20 C-atoms,
an alkenyl radical having 3-5 C-atoms,
an aralkyl radical having 7-12 C-atoms,
$-CH_2-CH_2-CN$,
$-CH_2-CH_2-COO-$alkyl,
$-CH_2-CH_2(CH_3)-COO-$alkyl an acyl radical or
$-(CH_2-CH_2O)_nH$, wherein n is 1-10 are stabilizers for synthetic resins, especially for polyolefins.

The cyclic imides of the general formula I can be prepared by the reaction of cyclic anhydrides or their corresponding acids with 4-amino-2,2,6,6-tetramethyl-piperidine.

The cyclic anhydrides which can be used include, for example, succinic anhydride, known alkyl or alkenyl succinic anhydrides and known Diels-Alder adducts of maleic anhydride and dienes such as butadiene, isoprene, piperylene, cyclopentadiene, trimethylcyclohexadiene, among others, and the corresponding hydrogenated Diels-Alder products.

These known piperidine compounds are unsatisfactory in stabilizing effect, and they are sufficiently volatile that they are lost from the polymer during processing at high temperatures, and they also are extracted by water.

In accordance with the present invention, bis-(2,2,6,6-tetramethyl-piperidyl)diimides are provided, having the formula:

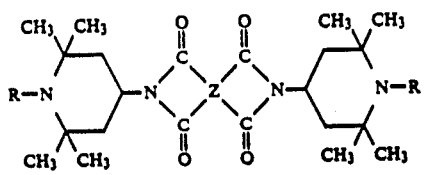

in which R is selected from the group consisting of hydrogen; oxyl; alkyl and alkenyl having from one to about eighteen carbon atoms; epoxy and hydroxyalkyl having from two to about eight carbon atoms; acyl having from two to about eight carbon atoms; and phenalkyl having from seven to about twelve carbon atoms; and Z is a tetravalent aliphatic or cycloaliphatic hydrocarbon group having from two to about eighteen carbon atoms; and stabilizer and synthetic polymer compositions containing such diimides having improved resistance to deterioration when exposed to light.

Exemplary R alkyl and alkenyl include methyl, ethyl, propyl, isopropyl, butyl, isobutyl, sec-butyl, tert-butyl, amyl, isoamyl, tert-amyl, hexyl, isohexyl, sec-hexyl, heptyl, octyl, isooctyl, 2-ethyl hexyl, tert-oxtyl, nonyl, isononyl, decyl, dodecyl, tetradecyl, and octadecyl and allyl.

Exemplary alkylphenyl include benzyl, α-phenylethyl, β-phenylethyl, γ-phenylpropyl and β-phenylbutyl.

Exemplary hydroxyalkyl include 2-hydroxyethyl, 2-hydroxypropyl, and 2-hydroxybutyl.

Exemplary epoxyalkyl include 2,3-epoxypropyl.

Exemplary acyl include acetyl, propionyl, butyroyl, acryloyl, methacryloyl, octanoyl and benzoyl.

Exemplary Z aliphatic hydrocarbon groups include ethylene, propylene, butylene, pentylene, hexylene, heptylene, octylene, nonylene, decylene, dodecylene, tetradecylene and octadecylene.

Exemplary Z cycloaliphatic hydrocarbon groups include cyclopentylene, cyclohexylene, cycloheptylene, and cyclooctylene.

Exemplary tetracarboxylic acids represented by the formula Z(COOH)₄ from which Z is derived include 1,2,3,4-butanetetracarboxylic acid and 1-methyl-3-(1',2'-dicarboxyethyl)-11-cyclohexene-5,6-dicarboxylic acid.

Examples of compounds represented by formula I are:

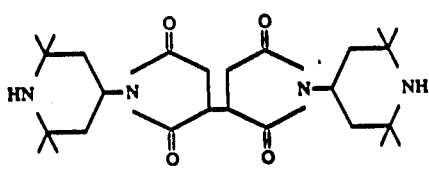

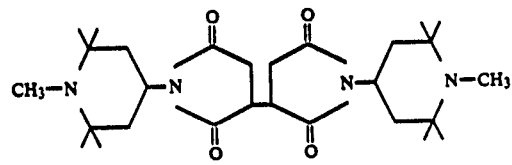

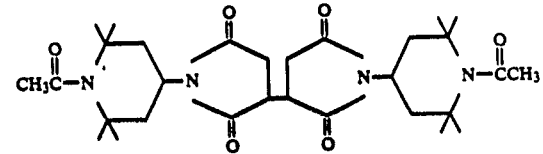

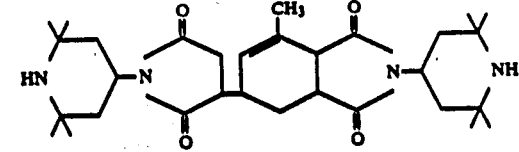

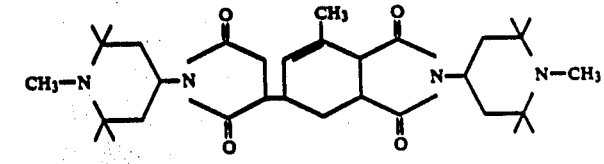

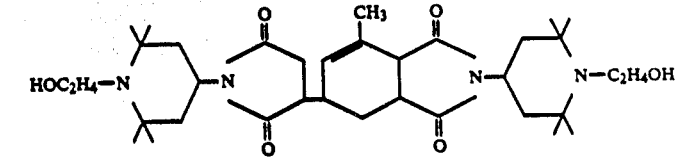

4,798,836

-continued

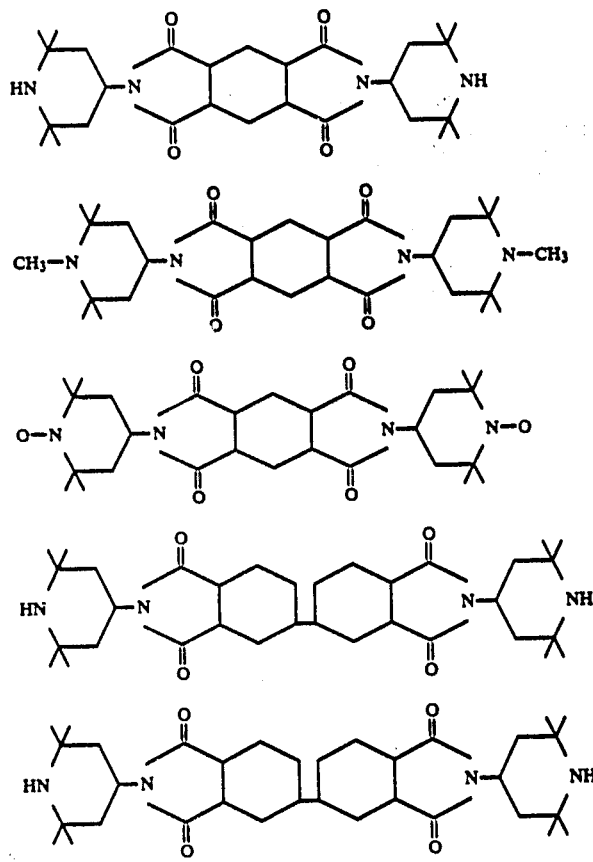

The compounds of formula (I) can be readily prepared by reacting 2,2,6,6-tetramethyl-4-piperidylamine with the corresponding dianhydride of the tetracarboxylic acid or ester of the tetracarboxylic acid, followed by alkylation or acylation, if desired.

EXAMPLE I

Preparation of

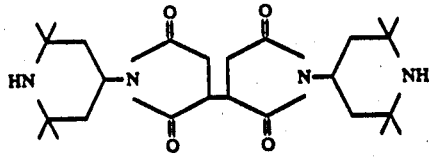

Tetramethyl-1,2,3,4-butanetetracarboxylate 5.80 g (0.02 mole) and 2,2,6,6-tetramethyl-4-piperidylamine 6.24 g (0.04 mole) were stirred for 3 hours at 210° C. under a stream of nitrogen. The product was dissolved in toluene, and washed with water, and then treated with active carbon. The active carbon was filtered off, and the solvent was distilled off, to obtain a white crystalline power melting at 266°–269° C.

I.R.: 1700 and 1770 cm$^{-1}$ (imide carbonyl)

EXAMPLE II

Preparation of

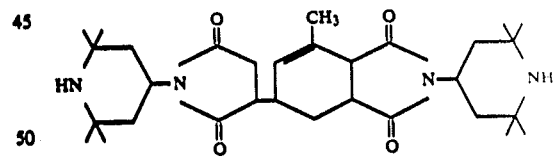

The anhydride of 1-methyl-3-(2,5-dioxotetrahydrofuryl)-1-cyclohexene-5,6-dicarboxylic acid 26.4 g (0.1 mole), 2,2,6,6-tetramethyl-4-piperidyl amine 34.3 g (0.22 mole) and dioxane 200 ml were stirred for one hour under reflux, and the precipitated white powder filtered off.

The precipitate, 81.6 g of acetic anhydride and 22.6 g of triethylamine were stirred for 8 hours at 80° C. The reaction mixture was poured into cold water, and then extracted with dichloroethane.

The dichloroethane solution was evaporated, obtaining a white powder melting at 65°–70° C.

I.R.: 1700 and 1770 cm$^{-1}$ (imide carbonyl)

EXAMPLE III

Preparation of

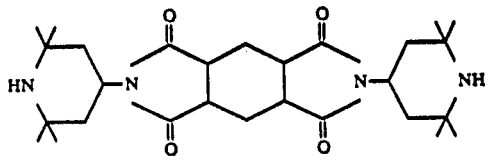

Cyclohexane 1,2,4,5-dianhydride 10.9 g was dissolved in 100 ml of tetrahydrofuran, and a solution of 15.6 g of 2,2,6,6-tetramethyl-4-piperidyl amine in tetrahydrofuran was added dropwise, at room temperature. The precipitated white crystals were filtered, and dried, and then dispersed in acetone. The tetrahydrate of nickel acetate 0.25 g, triethyl amine 6.1 g and acetic anhydride 12.8 g were added in, and stirred for 7 hours under reflux. The reaction mixture was poured into cold water, and then extracted with dichloroethane. The dichloroethane solution was evaporated, obtaining a white powder.

Small amounts of the bis-(piperidyl) diimides of this invention when combined with synthetic resin improve the light stability of the resin. The amount of the bis-(piperidyl)diimides is generally within the range from about 0.001 to about 5 parts by weight, preferably from about 0.01 to about 3 parts by weight, per 100 parts by weight of resin.

Synthetic resins that can have their resistance to deterioration enhanced with bis-(piperidyl) diimides according to this invention include α-olefin polymers such as polyethylene, polypropylene, polybutene, poly-3-methylbutene, or mixtures thereof and copolymers with other monomers such as ethylene-vinyl acetate copolymer; ethylene-propylene copolymer; polystyrene; polyvinyl acetate; polyacrylic esters; copolymers from styrene and another monomer (for example, maleic anhydride, butadiene, and acrylonitrile); acrylonitrile-butadiene-styrene copolymer, acrylic acid ester-butadiene-styrene copolymer, methacrylic acid ester-butadiene-styrene copolymer, polymethacrylate esters such as polymethacrylate; polyvinyl alcohol; polyvinyl formal; polyvinyl butyral; linear polyesters, polyamides; polycarbonates; polyacetals; polyurethanes, cellulosic resins; phenol-formaldehyde resins; urea-formaldehyde resins; melamine-formaldehyde resins; epoxy resins; unsaturated polyester resins; silicone resins; halogen-containing resins such as polyvinyl chloride, polyvinylidene chloride, polyvinylidene fluoride, and copolymers thereof, and rubbers such as isoprene rubber, butadiene rubber, epichlorohydrin rubber, chloroprene rubber, and blends of any of the above.

The bis-(piperidyl) diimides of the invention can be combined with conventional heat stabilizers such as phenolic antioxidants, polyvalent metal salts of organic acids, organic phosphites, thioethers, and other known heat stabilizers, thereby constituting light and heat stabilizer compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and

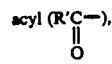

where R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

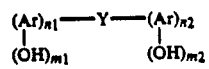

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condenses or separate phenyl rings; each Ar group contains at least one free phenolic hydroxyl group up to a total of five. The Ar rings can also include additional rings connected by additional linking nuclei of the type Y, for example, Ar—Y—AR—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine;

organic radicals containing from one to about thirty carbon atoms, such as alkyl, aryl, alkaryl, aralkyl, cycloalkenyl, cycloalkyl, alkoxy, aryloxy and

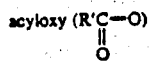

acyloxy (R'C=O)

where R' is aryl, alkyl or cycloalkyl, or thiohydrocarbon groups having from one to about thirty carbon atoms, and

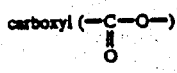

carboxyl (—C—O—)

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

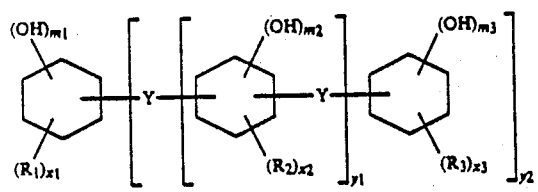

wherein $R_1$, $R_2$ and $R_3$ are inert substituent groups as described in the previous paragraph;

$m_1$ and $m_3$ are integers from one to a maximum of five;

$m_2$ is an integer from one to a maximum of four;

$x_1$ and $x_3$ are integers from zero to four, and $x_2$ is an integer from zero to three;

$y_1$ is an integer from zero to about six and $y_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as:

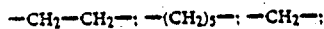

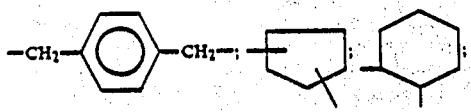

-continued

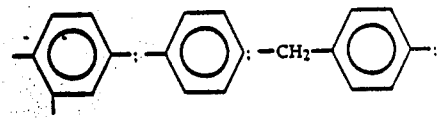

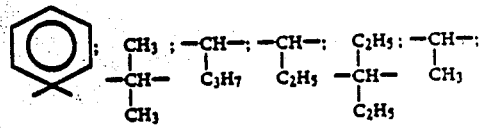

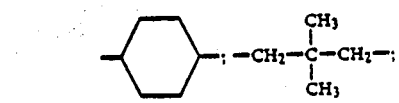

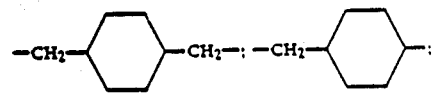

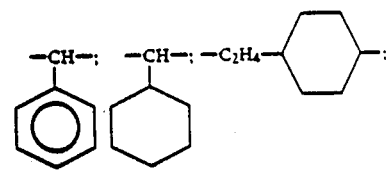

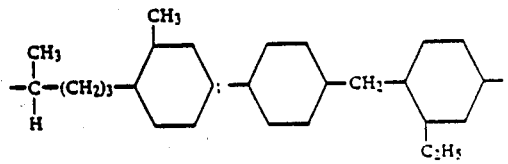

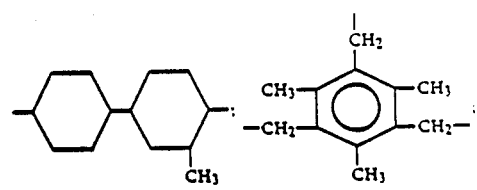

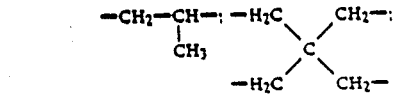

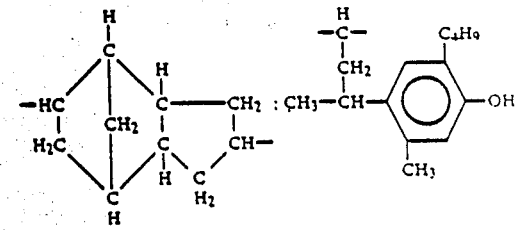

(2) Y groups where only atoms other than carbon link the aromatic rings, such as —O', —S—.

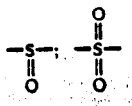

and —(S)$_x$— wherein x is a number from one to ten;

(3) Y groups made up of more than a single atom including both carbon and other atoms linking the aromatic nuclei, such as:

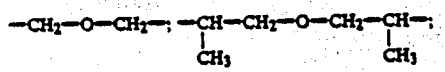

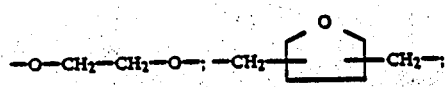

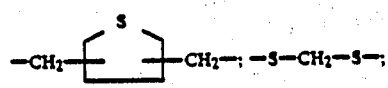

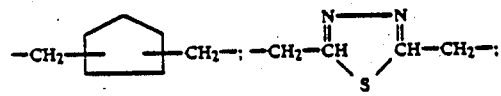

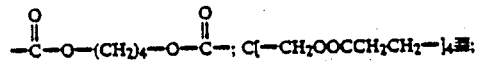

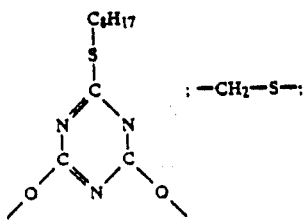

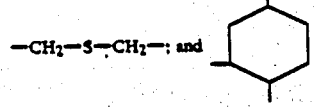

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenyl-phenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxy-phenol, p-n-decyloxy-cresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-dichlorobenzoyl-aminophenol, p-hydroxysalicyl anilide, stearyl-(3,5-di-methyl-4-hydroxy-benzyl) thioglycolate, stearyl-β-(4-hydroxy-3,5-di-t-butylphenyl) propionate, distearyl-3,5-di-t-butyl-4-hydroxybenzylphosphonate, and distearyl (4-hydroxy-3-methyl-5-methyl-5-t-butyl) benzylmalonate.

Exemplary polyhydric phenols are orcinol, propyl gallate, catechol, resorcinol, 4-octyl-resorcinol, 4-dodecyl-resorcinol, 4-octadecyl-catechol, 4-isooctyl-phloroglucinol, pyrogallol, hexahydroxybenzene, 4-isohexyl-catechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis(4-hydroxy phenyl)propane, methylene-bis-(p-cresol), 4,4'-benzylidene bis(2-tertiary-butyl-5-methyl-phenol), 4,4'-cyclo-hexylidene bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methyl-benzyl)-4-methylphenol, 4,4'-bis-(2-tertiary-butyl-5-methyl-phenol), 2,2'-bis-(4-hydroxy-phenyl) butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol, 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methyl-phenol), 2,2'-methylene-bis-(4-methyl-6-(1'-methyl-cyclohexyl)phenol), 4,4'-cyclohexylene bis-(2-tertiary-butyl-phenol), 2,6-bis-(2'-hydroxy-3'-t-butyl-5'-methyl-benzyl)-4-methyl-phenol, 4,4'-oxobis(naphthalene-1,5-diol), 1,3'-bis-(naphthalene-2,5-diol) propane, and 2,2'-butylene bis-(naphthalene-2,7-diol), (3-methyl-5-tert-butyl-4-hydroxyphenyl)-4'-hydroxy-phenyl) propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl) ethane, (2-hydroxy-phenyl)-(3',5'-di-tert-butyl-4',4-hydroxyphenyl) ethane, 2,2'-methylene-bis-(4-octylphenol), 4,4'-propylene-bis-(2-tert-butyl-phenol), 2,2'-isobutylene-bis-(4-nonylphenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis(3-t-butyl-4-hydroxyphenyl) thiazolo-(5,4-d) thiazole, 2,2'-bis-(3-methyl-5-t-butyl-4-hydroxyphenyl) thiazolo-(5,4-d)-thiazole, 4,4'-bis-(4-hydroxyphenyl) pentanoic acid octadecyl ester, cyclopentylene-4,4'-bis-phenol, 2-ethylbutylene-4,4'-bisphenol, 4,4'-cyclooctylene-bis-(2-cyclohexylphenol), β,β-thiodiethanol-bis-(3-tert-butyl-4-hydroxyphenoxy acetate), 1,4-butanedio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl) sulfide, bis-(2-tert-butyl-4-hydroxy-5-methylphenyl) sulfide, bis-(2-tert-butyl-4-hydroxy-5-methylphenyl) sulfoxide, bis-(3-ethyl-5-tert-butyl-4-hydroxybenzyl) sulfide, bis-(2-hydroxy-4-methyl-6-tert-butyl-phenyl) sulfide, 4,4'-bis-(4-hydroxyphenol) pentanoic acid octadecyl thiopropionate ester, 1,1,3-tris-(2'-methyl-4-hydroxy-5'-tert-butylphenyl) butane, 1,1,3-tris-(1-methyl-3-hydroxy-4-tert-butylphenyl) butane, 1,8-bis-(2-hydroxy-5-methyl-benzoyl-n-octane, 2,2'-ethylene-bis-[4'-(3-tert-butyl-4- hydroxyphenyl)-thiazole], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butylphenyl) butyric acid] glycol ester, 4,4'-butylidene-bis-(6-t-butyl-m-cresol), 1,1,3-tris-(2-methyl-4-hydroxy-5-t-butylphenyl) butane, 1,3,5-tris-(3,5-di-t-butyl-4-hydroxybenzyl)-2,4,6-trimethylbenzene, tetrakis [methylene-3 (3,5-di-t-butyl-4-hydroxyphenyl)propionate] methane, 1,3,5-tris-(3,5-di-t-butyl-4-hydroxybenzyl) isocyanurate, 1,3,5-tris-(3,5-di-t-butyl-4-hydroxyphenyl) propionyl-oxyethyl isocyanurate, 2-octylthio-4,6-di-(4-hydroxy-3,5-di-t-butyl) phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicyclopentadiene polyphenols, which are of the type:

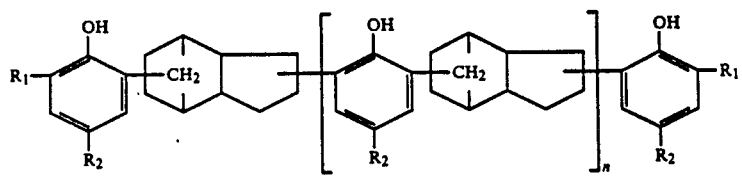

in which $R_1$ and $R_2$ are lower alkyl, and can be the same or different, and n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

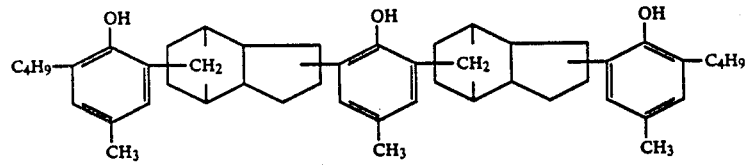

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. No. 3,124,555, U.S. Pat. No. 3,242,135, and British Pat. No. 961,504.

When the bis-(piperidyl) diimide is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophisphites.

The organic triphosphites in which the radicals are monovalent radicals can be defined by the formula:

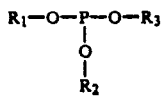

in which $R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

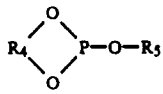

in which $R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$, and $R_3$;

$R_5$ is hydrogen or a cation, in the case of the acid phosphites.

Also useful organic triphosphites are mixed heterocyclic-open chain phosphites of the type:

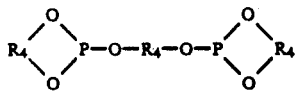

More complex triphosphites are formed from trivalent organic radicals, of the type:

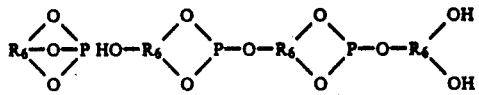

in which $R_6$ is a trivalent organic radical of any of the types of $R_1$ to $R_5$, inclusive, as defined above.

A particularly useful class of complex triphosphites are the tetraoxadiphosphaspiro undecanes of the formula:

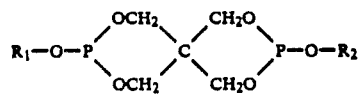

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula:

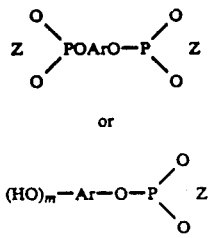

in which

Ar is a mono or bicyclic aromatic nucleus and m is an integer of from 0 to about 5. Z is one or a plurality of organic radicals as defined above for $R_1$ to $R_6$, taken singly or together in sufficient number to satisfy the valences of the two phosphite oxygen atoms.

One or both Z radicals is also hydrogen, in the case of the acid phosphites, and can include additional bicyclic aromatic groups of the type $(HO)_m$—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl)phosphite, trioctadecyl phosphite, triisooctyl phosphite, tridodecyl phosphite, isooctyl diphenyl phosphite, diisooctyl phenyl phosphite, tri(t-octylphenyl)phosphite, tri-(t-nonylphenyl)phosphite, benzyl methyl isopropyl phosphite, butyl dicresyl phosphite, isooctyl di(octylphenyl)phosphite, di(2-ethylhexyl)(isooctylphenyl)phosphite, tri(2-cyclohexylphenyl)phosphite), tri-α-naphthyl phosphite, tri(-phenylphenyl)phosphite, tri(2-phenylethyl)phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane(diphenyl-pentaerythritol diphosphite), 3,9-di(decyloxy)-2,4,8,10-tetraoxa-3,9-diphosphaspiro(5,5)-undecane, 3,9-di(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(butoxyethoxyethyloxy)-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane where the (polyethoxy)ethyloxy group has an average molecular weight of 350), 3,9-di(methoxy(polyethoxy)ethyloxy)-2,4,8,10-tetraoxa-3,9-diphosphaspiro-(5,5)-undecane (where the (polyethoxy)ethyloxy group has an average molecular weight of 550).

Exemplary of the bis aryl triphosphites are: bis(4,4'-thio-bis(2-tertiary-butyl-5-methyl-phenol))isooctyl phosphite, mono(4,4'-thio-bis(2-tertiary-butyl-5-methylphenol))di-phenyl phosphite, tri-(4,4'-n-butylidene-bis(2-tertiary-butyl-5-methylphenol))phosphite, (4,4'-benzylidene-bis(2-tertiary-butyl-5-methyl-phenol))diphenyl phosphite, isooctyl 2,2'-bis(-parahydroxyphenyl)propane phosphite, decyl 4,4'-n-butylidene-bis(2-tertiary-butyl-5-methylphenol)phosphite, tri-4,4'-thio-bis(2-tertiary-butyl-5-methylphenol)phosphite, 2-ethylhexyl-2,2'-methylene-bis(4-methyl-6,1'-methylcyclohexyl)phenol phosphite, tri(2,2'-bis-(para-hydroxyphenyl)propane)phosphite, tri(4,4'-thio-bis(2-tertiary-butyl-5-methyl-phenol)phosphite, isooctyl(2,6-bis(2'-hydroxy-3,5-dinonylbenzyl)-4-nonyl phenyl))phosphite, tetra-tridecyl-4,4'-n-butylidene-bis(2-tertiary-butyl-5-methylphenyl)diphosphite, tetra-isooctyl-4,4'-thio-bis(2-tertiary-butyl-5-methylphenyl)diphosphite, 2,2'-methylene-bis(4-methyl-6,1'-methyl cyclohexyl phenyl)polyphosphite, isooctyl-4,4'-isopropylidene-bis-phenyl polyphosphite, 2-ethylhexyl-2,2'-methylene-bis(4-methyl-6,1'-methyl-cyclohexyl)phenyl triphosphite, tetra-tridecyl-4,4'-oxydiphenyl diphosphite, tetra-n-dodecyl-4,4'-n-butylidene bis(2-tertiary-butyl-5-methylphenyl)diphosphite, tetra-tridecyl-4,4'-isopropylidene bisphenyl diphosphite, hexa-tridecyl butane-1,1,3-tris(2'-methyl-5'-tertiary-butylphenyl-4')triphosphite.

Exemplary acid phosphites are di(phenyl)phosphite, monophenyl phosphite, mono(diphenyl)phosphite, dicresyl phosphite, di-(o-isooctylphenyl)phosphite, di(p-ethylhexylphenyl)phosphite, di(p-t-octylphenyl)-phosphite, di(dimethylphenyl)phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl)phosphite, monocyclohexyl phosphite, dicyclohexyl phosphite, di(2-cyclohexyl phenyl)phosphite, di-α-naphthyl phosphite, diphenyl phenyl phosphite, di(diphenyl)phosphite, di-(2-phenyl ethyl)phosphite, dibenzyl phosphite, monobenzyl phosphite, n-butyl cresyl phosphite and didodecyl phosphite, cresyl phosphite, t-octylphenyl phosphite, ethylene phosphitem, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenol))-phosphite, (4,4'-thio-bis(2-tertiary-butyl-5-methylphenol))phenyl phosphite, bis(4,4'-n-butylidene-bis(2-tertiary-butyl-5-methylphenol))phosphite, mono(4,4'-benzylidene-bis(2-tertiary-butyl-5-methylphenol))-phosphite, mono(2,2'-bis-(parahydroxyphenyl)-propane)phosphite, mono(4,4'-butylidene-bis(2-tertiary-butyl-5-methylphenol)phosphite, bis(4,4'-thio-bis(2-tertiary-butyl-5-methylphenol))phosphite, mono-2-ethylhexyl-mono-2,2'-methylene-bis(4-methyl-6,1'-methyl-cyclohexyl)phenol phosphite, bis(2,2'-bis(para-hydroxyphenyl)propane)phosphite, monoisooctylmono(4,4'-thio-bis(2-tertiary-butyl-5-methylphenol))phosphite, isooctyl-(2,6-bis(2'-hydroxy-3,5-dinonylbenzyl)-4-nonylphenyl))phosphite, tri-tridecyl-4,4'-n-butylidene-bis(2-tertiary-butyl-5-methylphenyl)diphosphite, trii-sooctyl-4,4'-thio-bis(2-tertiary-butyl-5-methylphenyl)-diphosphite, bis(2,2'-methylene-bis(4-methyl-6,1'-methyl cyclohexyl phenyl))phosphite, isooctyl-4,4'-isopropylidene-bis-phenyl phosphite, monophenyl mono(2,2'-methylene-bis(4-methyl-6,1'-methyl-cyclohexyl))triphosphite, di-tridecyl-4,4'-oxydiphenyl diphosphite, di-n-dodecyl-4,4'-n-butylidene-bis(2-tertiary-butyl-5-methylphenyl)diphosphite, di-tridecyl-4,4'-isopropylidene bisphenyl diphosphite, tetra-tridecyl butane-1,1,3-tris(2'-methyl-5-tertiary-butylphenyl-4)-triphosphite.

The thiodipropionic acid ester has the following formula:

$R_1OOCCH_2CH_2-S-CH_2CH_2COOY$ in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

$-XO[OCCH_2CH_2SCH_2CH_2COOXO]_nOCCH_2CH_2-S-CH_2CH_2COOZ$ where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylene-arylene and mixed alkylene-cycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming within the above-designated categories within the general formula can be defined as follows:

(a) R₁OOCCH₂CH₂SCH₂CH₂COOH
(b) R₁OOCCH₂CH₂SCH₂CH₂COOR₂
(c) R₁O[OCCH₂CH₂SCH₂CH₂COOX—O]-ₙOCCH₂CH₂SCH₂CH₂COOZ
(d) R₁OOCCH₂CH₂SCH₂CH₂COOM

In the above formulae R₁ and R₂, M, X and Z are the same as before and the value of $n_1$ can range upwards from 1, but there is no upper limit on $n_1$ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, R₂ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as 1,2-propylene,

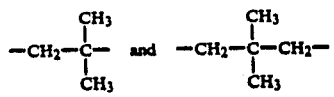

arylene radicals such as phenylene

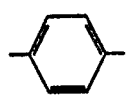

methylenephenylene

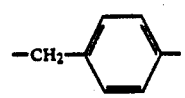

dimethylene phenylene

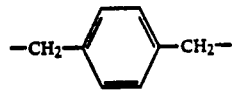

and alicyclylene such as cyclohexylene

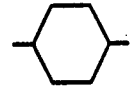

and cyclopentylene

As exemplary of the thiodipropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl)thiodipropionic acid.

These esters are for the most part known compounds, but where they are not available, they are readily prepared by esterification of thiodipropionic acid and the corresponding alcohol.

Also useful are:

(1) Thioalkanoic acid amides of Tokuno et al Japanese Pat. No. 16,286/68 having the formula:

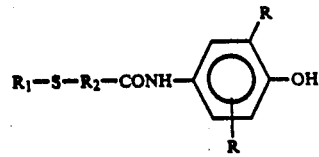

R is alkyl of one to eight carbon atoms, R₁ is alkyl of six to twenty-four carbon atoms, and R₂ is alkylene of one to six carbon atoms.

(2) Thioalkanoic acid amides of 1,3,5-triazines of Ozeki et al Japanese Pat. No. 20,366/68 having the formula:

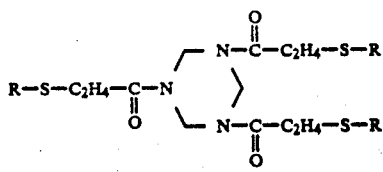

R is alkyl of eight to eighteen carbon atoms.

(3) Bis-thioalkanoic acid amides of Yamamoto et al Japanese Pat. No. 23,765/68 having the formula:

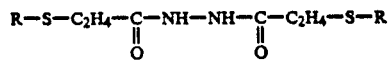

R is alkyl of more than six carbon atoms, aryl or aralkyl.

(4) Bis-thioalkylanoic acid amides of Ozeki et al Japanese Pat. No. 26,184/69 having the formula:

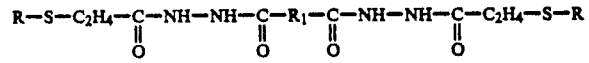

R is alkyl of twelve to eighteen carbon atoms, and $R_1$ is alkylene of one to ten carbon atoms, cycloalkylene, or arylene.

(5) Bis-alkylene thioalkanoic acid amides of Ozeki Japanese Pat. No. 31,464/69 having the formula:

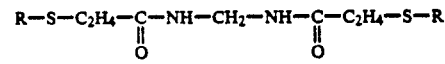

R is alkyl of more than six carbon atoms, aryl, or aralkyl.

(6) Thioalkanoic acid amide derivatives of Minagawa et al, published Japanese application No. 106,484/74 having the formula:

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

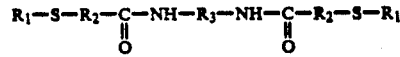

wherein:
$R_1$ is alkyl having from one to about fifty carbon atoms;
$R_2$ is alkylene having from one to about three carbon atoms; and
$R_3$ is alkylene having from about two to about twelve carbon atoms.

β-Alkylthiopropionic acid esters having the general formula:

$R-S-C_2H_4COOR+R')_n$ wherein:
R is alkyl of four to twenty carbon atoms;
n is a number from 1 to 6; and
R' is the residue of an alcohol having from one to six hydroxyl groups.

Pentaerythritol tetra dodecyl thiopropionate is an example of this group.

Other conventional light stabilizers can be employed, such as hydroxybenzophenones such as 2-hydroxy-4-methoxybenzophenone, 2-hydroxy-4-n-octoxybenzophenone, 2,2'-dihydroxy-4-methoxybenzophenone and 2,4-dihydroxybenzophenone; benzotriazoles such as 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-5'-methylphenyl)benzotriazole and 2-(2'-hydroxy-3',5'-di-t-amylphenyl)benzotriazole; benzoates such as phenyl salicylate, p-t-butylphenyl salicylate, 2,4-di-t-butylphenyl-3,5-di-t-butyl-4-hydroxybenzoate and hexadecyl-3,5-di-t-butyl-4-hydroxybenzoate; Ni compounds such as 2,2'-thiobis(4-t-octylphenol)Ni salt, (2,2'-thiobis(4-t-octylphenolate))-n-butylamine Ni and (3,5-di-t-butyl-4-hydroxybenzyl)phosphonic acid monoethyl ester Ni salt; substituted acrylonitriles such as α-cyano-β-methyl-β-(p-methoxyphenyl)acrylic acid methyl ester; and oxanilides such as N-2-ethylphenyl-N'-2-ethoxy-5-t-butylphenyloxanilide and N-2-ethylphenyl-N'-2-ethoxyphenyloxanilide.

A sufficient amount of the stabilizer or combination is used to improve the resistance of the synthetic polymer to deterioration in physical properties when exposed to heat and light, including, for example, discoloration, reduction in melt viscosity and embrittlement. Very small amounts are usually adequate. Amounts within the range from about 0.001 to about 5% total stabilizers including the bis-(piperidyl)diimides of the invention by weight of the polymer are satisfactory. Preferably, from 0.01 to 3% is employed for optimum stabilization.

The stabilizer systems of the invention are readily rendered in solid particulate form, comprising a blend of:
(a) bis-(piperidyl)diimide light stabilizer in an amount of from about 10 to about 35 parts by weight;
and optionally;
(b) a phenolic antioxidant in an amount from about 10 to about 35 parts by weight; and/or
(c) other heat or light stabilizers in an amount of from about 10 to about 35 parts by weight.

The bis-(piperidyl)diimide light stabilizer of the invention can be employed in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds; and organic phosphites.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadiene-styrene terpolymers, other antioxidants and polyvalent metal salts of the higher fatty acids can be used.

In addition, other conventional additives for synthetic polymers, such as heavy metal deactivators, nucleating agents, plasticizers, lubricants, emulsifiers, antistatic agents, processing aids, blowing agents, flameproofing agents, pigments and fillers, can be employed.

The stabilizer or combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The polymer materials stabilized with the stabilizer of the invention can be any physical forms, including filaments, yarns, films, sheets, molded articles, latex, foams and coatings.

The following Examples represent preferred embodiments of stabilizer and synthetic polymer compositions of the invention.

EXAMPLES 1 TO 3

Polypropylene compositions were prepared, using stabilizers of the invention and two of the prior art and having the following formulation:

| Ingredient | Parts by Weight |
|---|---|
| Polypropylene | 100 |
| Tetrakis (methylene-3-(3,5-di-t-butyl-4-hydroxyphenyl) propionate) methane | 0.1 |
| Calcium stearate | 0.05 |
| Diimide stabilizer as shown in Table I | 0.3 |

The compositions were thoroughly blended in a Brabender Plastograph, and then compression-molded to form sheets 0.3 mm thick. Pieces 2.5 cm$^2$ were cut off from the sheets and exposed to a high pressure mercury lamp with and without immersion in hot water at 80° C. for 15 hours.

The hours to failure were noted, and shown in Table I.

TABLE I

| | | Hours to Failure | |
|---|---|---|---|
| Example No. | Stabilizer | Without Immersion | After Immersion |
| Control 1 | Bis(2,2,6,6-tetramethyl-4-piperidyl)sebacate | 480 | 390 |
| Control 2 | N—(2,2,6,6-tetramethyl-4-piperidyl)dodecylsuccinimide | 410 | 360 |
| Example 1 | [structure] | 710 | 670 |
| Example 2 | [structure] | 680 | 650 |
| Example 3 | [structure] | 660 | 620 |

The superiority of the bis-imides of the invention to the monoimide of Control 2 (U.S. Pat. No. 4,356,307, compound of Example 1) is apparent.

EXAMPLES 4 TO 9

Conventional stabilizers for polymeric materials may lose their effectiveness because of volatilization or decomposition at high polymer processing temperature. This is not true of the stabilizers of the invention, as shown by observing the effect of heat in repeated extrusions of ethylene-propylene copolymer compositions.

These compositions were prepared using stabilizers of the invention and of the prior art, and having the following formulation:

| Ingredient | Parts by Weight |
|---|---|
| Ethylene-propylene copolymer | 100 |
| Calcium stearate | 0.2 |
| aryl-β-(3,5-di-t-butyl-4-hydroxyphenyl) propionate | 0.1 |
| Dilauryl thiodipropionate | 0.2 |
| Diimide stabilizer as shown in Table II | 0.2 |

The ingredients were mixed and the compositions then extruded five times. (Cylinder temperature 230° C. and 240° C., head die temperature 250° C., velocity 20 rpm). Test pieces were then molded by injection molding at 250° C. The test pieces were exposed to a high pressure mercury lamp, and the hours to failure were noted. The results are shown in Table II.

The superiority of the bis-imides of the invention to the monoimide of Control 2 (U.S. Pat. No. 4,356,307, compound of Example 1) is apparent.

EXAMPLES 10 TO 13

High density polyethylene compositions were prepared, using the stabilizers of the invention and two of the prior art, and having the following formulation:

| Ingredient | Parts by Weight |
|---|---|
| High-density polyethylene | 100 |
| Calcium stearate | 1 |
| Tetrakis (methylene-3-(3,5-di-t-butyl-4-hydroxyphenyl) propionate) methane | 0.1 |
| Distearyl thiodipropionate | 0.3 |

TABLE II

| Example No. | Stabilizer | Hours to Failure | | |
|---|---|---|---|---|
| | | Extruded One Time | Extruded Five Times | Extruded Ten Times |
| Control 1 | Bis(2,2,6,6-tetramethyl-4-piperidyl)sebacate | 490 | 430 | 380 |
| Control 2 | N—(2,2,6,6-tetramethyl-4-piperidyl)dodecylsuccinimide | 460 | 410 | 370 |
| Example 4 | [structure] | 620 | 580 | 550 |
| Example 5 | [structure] | 600 | 560 | 520 |
| Example 6 | [structure] | 620 | 590 | 550 |
| Example 7 | [structure] | 600 | 560 | 530 |
| Example 8 | [structure] | 600 | 560 | 540 |
| Example 9 | [structure] | 550 | 510 | 490 |

-continued

| Ingredient | Parts by Weight |
|---|---|
| Diimide stabilizer as shown in Table III | 0.2 |

The stabilizers were blended with the polymer on a two-roll mill and sheets 0.5 mm thick were prepared by compression-molding of the blend. Pieces 2.5 cm² were cut off from the sheets, and exposed in a Weather-O-Meter to ultraviolet light. The time in hours when degradation set in, as determined by a significant discoloration and/or embrittlement, was noted as hours to failure, and the results are reported in Table III.

| Ingredient | Parts by Weight |
|---|---|
| Polyvinyl chloride | 100 |
| Dioctyl phthalate | 48 |
| Epoxidized soybean oil | 2 |
| Tris(nonyl phenyl) phosphite | 0.2* |
| Calcium stearate | 1.0 |
| Zinc stearate | 0.1 |
| Diimide stabilizer as shown in Table IV | 0.2 |

The formulations were blended and sheeted off on a two-roll mill to form sheets 1 mm thick. The light resistance of these sheets was then determined by placing

TABLE III

| Example No. | Stabilizer | Hours to Failure |
|---|---|---|
| Control 1 | Bis(2,2,6,6-tetramethyl-4-piperidyl)sebacate | 1020 |
| Control 2 | N—(2,2,6,6-tetramethyl-4-piperidyl)dodecylsuccinimide | 980 |
| Example 10 | [structure] | 1270 |
| Example 11 | [structure] | 1300 |
| Example 12 | [structure] | 1250 |
| Example 13 | [structure] | 1250 |

The superiority of the bis-imides of the invention to the monoimide of Control 2 (U.S. Pat. No. 4,356,307, compound of Example 1) is apparent.

EXAMPLES 14 TO 18

A group of polyvinyl chloride resin compositions was prepared, having the following formulation:

strips 1 cm wide in a Weather-O-Meter, and exposing them to ultraviolet light. The time in hours was then noted for the sheets to develop a noticeable discoloration and/or embrittlement, indicating deterioration due to oxidation in the presence of ultraviolet light. The results obtained are shown in Table IV.

TABLE IV

| Example No. | Stabilizer | Hours to Failure |
|---|---|---|
| Control 1 | None | 180 |
| Control 2 | Bis(2,2,6,6-tetramethyl-4-piperidyl) sebacate | 350 |
| Control 3 | N—(2,2,6,6-tetramethyl-4-piperidyl) dodecylsuccinimide | 430 |
| Example 14 | [structure] | 580 |

TABLE IV-continued

| Example No. | Stabilizer | Hours to Failure |
|---|---|---|
| Example 15 | [structure: bis-imide with two N-CH₃ tetramethylpiperidyl groups linked through two succinimide rings] | 550 |
| Example 16 | [structure: bis-imide with two CH₃C(O)-N tetramethylpiperidyl groups linked through two succinimide rings] | 560 |
| Example 17 | [structure: bis-imide with two HN tetramethylpiperidyl groups linked through two imide rings on a methylcyclohexene] | 570 |
| Example 18 | [structure: bis-imide with two CH₃-N tetramethylpiperidyl groups linked through two imide rings on a methylcyclohexene] | 540 |

The superiority of the bis-imides of the invention to the monoimide of Control 2 (U.S. Pat. No. 4,356,307, compound of Example 1) is apparent.

EXAMPLES 19 TO 22

Polyurethane resin compositions were prepared using stabilizers of the invention and of the prior art, and having the following formulation:

| Ingredient | Parts by Weight |
|---|---|
| Polyurethane resin (Asahi Denka U-100) | 100 |
| Ba stearate | 0.7 |
| Zn stearate | 0.3 |
| 2,6-di-t-butyl-p-cresol | 0.1 |
| Diimide stabilizer as shown in Table V | 0.3 |

The stabilizers were blended with the finely powdered polyurethane resin on a two-roll mill for five minutes at 70° C., and the sheet was then compression-molded at 120° C. for five minutes to form sheets 0.5 mm thick. Pieces 2.5 cm² were cut out from the sheets, and exposed to ultraviolet light in a Weather-O-Meter.

Elongation before and after exposure was determined, and the percent elongation retained after the exposure is given in Table V.

TABLE V

| | | % Retention of Elongation | |
|---|---|---|---|
| Example No. | Stabilizer | After 50 hours | After 100 hours |
| Control 1 | Bis(2,2,6,6-tetramethyl-4-piperidyl) sebacate | 68 | 52 |
| Control 2 | N—(2,2,6,6-tetramethyl-4-piperidyl) dodecylsuccinimide | 64 | 44 |
| Example 19 | [structure: bis-imide with two HN tetramethylpiperidyl groups linked through two succinimide rings] | 77 | 69 |

TABLE V-continued

| Example No. | Stabilizer | % Retention of Elongation | |
| --- | --- | --- | --- |
| | | After 50 hours | After 100 hours |
| Example 20 | [structure: CH₃—N-piperidyl—N-succinimide-succinimide—N-piperidyl—N—CH₃] | 77 | 70 |
| Example 21 | [structure: HN-piperidyl—N-imide-cyclohexene(CH₃)-imide—N-piperidyl—NH] | 75 | 65 |
| Example 22 | [structure: HOC₂H₄—N-piperidyl—N-imide-cyclohexene(CH₃)-imide—N-piperidyl—N—C₂H₄OH] | 74 | 63 |

The superiority of the bis-imides of the invention to the monoimide of Control 2 (U.S. Pat. No. 4,356,307, compound of Example 1) is apparent.

EXAMPLES 23 TO 27

The stabilizers of this invention are effective as light stabilizer for coatings.

The effect of the stabilizer in a two-coat metallic effect finish comprising metallic effect priming lacquer and unpigmented finishing lacquer was determined.

(a) Metallic effect priming lacquer

Methyl methacrylate 100 g, n-butylacrylate 66 g, 2-hydroxyethyl-methacrylate 30 g, methacrylic acid 4 g, xylene 80 g and n-butanol 20 g were heated and stirring at 110° C. and a solution of azobisisobutyronitrile 2 g, dodecylmercaptan 0.5 g, xylene 80 g and n-butanol 20 g was added dropwise over 3 hours. The solution was stirred an additional 2 hours at 110° C. thus obtaining an acrylic resin solution.

The above acrylic resin solution 12 parts, butoxylated methylol-melamine (Mitsui-Toatsu Co., Yuban 20SE60; solids content 60%) 2.5 parts, cellulose acetobutyrate (20% butylacetate solution) 50 parts, aluminum pigment (Toyo Aluminum Co., Alpaste 1123N) 5.5 parts, xylene 10 parts, butyl acetate 20 parts and copper phthalocyanine blue 0.2 parts were blended.

(b) Unpigmented finishing lacquer

The above acrylic resin solution 48 parts, butoxylated methylol-melamine 10 parts, xylene 10 parts, butoxyethyl acetate 1 part and 0.15 part of the stabilizer as shown in Table VI were blended.

Pieces of steel sheeting, which were coated with a primer, were first coated with the priming lacquer, and subsequently with the finishing lacquer. The priming lacquer was sprayed on to a thickness of about 20μ, and air-dried for 10 minutes. Then the clear lacquer was sprayed on to a thickness of about 30μ. After being air-dried for 15 minutes, the samples were heated in an oven for 30 minutes at 140° C.

The coated sheets were exposed to ultraviolet light in a Weather-O-Meter. The time in hours when degradation set in, as determined by a cracking on a surface of sheet, was noted as hours to failure, and the results are shown in Table VI.

TABLE VI

| Example No. | Stabilizer | Hours to Failure |
| --- | --- | --- |
| Control 1 | None | 1600 |
| Control 2 | Bis(2,2,6,6-tetramethyl-4-piperidyl) sebacate | 2200 |
| Control 3 | N—(2,2,6,6-tetramethyl-4-piperidyl) dodecylsuccinimide | 2300 |
| Example 23 | [structure: HN-piperidyl—N-succinimide-succinimide—N-piperidyl—NH] | 3400 |

TABLE VI-continued

| Example No. | Stabilizer | Hours to Failure |
|---|---|---|
| Example 24 | | 3200 |
| Example 25 | | 3300 |
| Example 26 | | 3500 |
| Example 27 | | 3300 |

The superiority of the bis-imides of the invention to the monoimide of Control 2 (U.S. Pat. No. 4,356,307, compound of Example 1) is apparent.

Having regard to the foregoing disclosure, the following is claimed as the inventive and patentable embodiments thereof:

1. Bis-(2,2,6,6-tetramethyl-piperidyl)diimides having the formula:

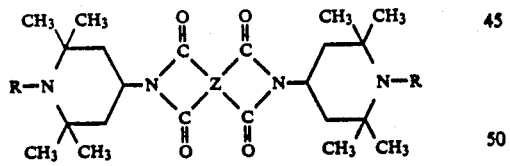

in which R is selected from the group consisting of hydrogen; oxyl; alkyl and alkenyl having from one to about eighteen carbon atoms; epoxy and hydroxyalkyl having from two to about eight carbon atoms; acyl having from two to about eight carbon atoms; and phenalkyl having from seven to about twelve carbon atoms; and Z is a tetravalent aliphatic or cycloaliphatic hydrocarbon group having from two to about eighteen carbon atoms.

2. Bis-(2,2,6,6-tetramethyl-piperidyl)diimides according to claim 1 in which Z is a tetravalent aliphatic hydrocarbon group.

3. Bis-(2,2,6,6-tetramethyl-piperidyl)diimides according to claim 1 in which Z is a tetravalent cycloaliphatic hydrocarbon group.

4. Bis-(2,2,6,6-tetramethyl-piperidyl)diimides according to claim 1 in which Z is 1,2,3,4-butylene.

5. Bis-(2,2,6,6-tetramethyl-piperidyl) diimides according to claim 1 in which Z is 1-methyl-3-(1',2'-diimidoethyl)5,6-diimido-11-cyclohexene.

6. Bis-(2,2,6,6-tetramethyl-piperidyl)diimides according to claim 1 having the formula

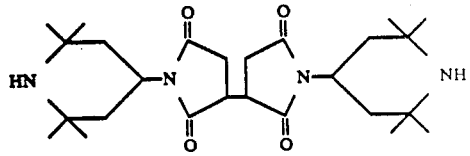

7. Bis-(2,2,6,6-tetramethyl-piperidyl)diimides according to claim 1 having the formula

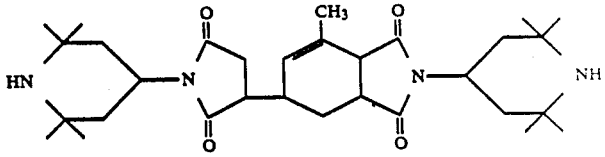

8. A stabilizer composition for synthetic resins comprising:
   (1) at least one bis-(2,2,6,6-tetramethyl piperidyl)diimide in accordance with claim 1 and
   (2) at least one heat stabilizer for synthetic polymers selected from the group consisting of organic phosphites, polyvalent metal salts of organic carboxylic acids, thiodipropionates, and phenolic antioxidants having at least one phenolic hydroxyl group, and at least one phenolic nucleus, and from about eight to about three hundred carbon atoms.

9. A polyvinyl chloride resin composition having improved resistance to deterioration comprising a polyvinyl chloride resin and bis-(2,2,6,6-tetramethyl piperidyl)diimide in accordance with claim 1.

10. A polyvinyl chloride resin composition in accordance with claim 9 in which the polyvinyl chloride resin is polyvinyl chloride homopolymer.

11. A polyvinyl chloride resin composition in accordance with claim 9 in which the polyvinyl chloride resin is a copolymer of vinyl chloride and vinyl acetate.

12. An olefin polymer composition having improved resistance to deterioration comprising an olefin polymer selected from the group consisting of polymers of alpha-olefins having from two to six carbon atoms and polystyrene, and bis-(2,2,6,6-tetramethyl piperidyl)diimide in accordance with claim 1.

13. An olefin polymer composition in accordance with claim 12 wherein the polyolefin is polypropylene.

14. An olefin polymer composition in accordance with claim 12 wherein the polyolefin is polyethylene.

15. An olefin polymer composition in accordance with claim 12 wherein the polyolefin is ethylene-propylene copolymer.

16. A polyurethane resin composition having improved resistance to deterioration comprising a polyurethane resin and bis-(2,2,6,6-tetramethyl piperidyl)diimide in accordance with claim 1.

* * * * *